US008886274B2

(12) United States Patent
Gericke et al.

(10) Patent No.: US 8,886,274 B2
(45) Date of Patent: Nov. 11, 2014

(54) NON-INVASIVE METHOD FOR ESTIMATING OF THE VARIATION OF THE GLUCOSE LEVEL IN THE BLOOD OF A PERSON AND APPARATUS FOR CARRYING OUT THE METHOD

(75) Inventors: Monica Gericke, Zollikon (CH); Boris A. Paramonov, St. Petersburg (RU); Ivan Ivanovich Turkovskiy, St. Petersburg (RU)

(73) Assignee: Gerinova AG, Stans (CH)

( * ) Notice: Subject to any disclaimer, the term of this patent is extended or adjusted under 35 U.S.C. 154(b) by 906 days.

(21) Appl. No.: 12/737,908

(22) PCT Filed: Aug. 26, 2009

(86) PCT No.: PCT/EP2009/006178
§ 371 (c)(1),
(2), (4) Date: Apr. 25, 2011

(87) PCT Pub. No.: WO2010/022926
PCT Pub. Date: Mar. 4, 2010

(65) Prior Publication Data
US 2011/0224521 A1    Sep. 15, 2011

(30) Foreign Application Priority Data

Aug. 29, 2008 (EP) .................................. 08015256
Nov. 3, 2008 (EP) .................................. 08019159

(51) Int. Cl.
*A61B 5/05* (2006.01)
*A61B 5/145* (2006.01)
*A61B 5/053* (2006.01)
*A61B 5/00* (2006.01)
*A61B 5/03* (2006.01)

(52) U.S. Cl.
CPC . *A61B 5/681* (2013.01); *A61B 5/03* (2013.01);
*A61B 5/14532* (2013.01); *A61B 2560/0252* (2013.01); *A61B 5/053* (2013.01); *A61B 5/4519* (2013.01)
USPC ........................... 600/345; 600/347; 600/365

(58) Field of Classification Search
CPC . A61B 5/14532; A61B 5/1468; A61B 5/1477
USPC .......................................... 600/345, 347, 365
See application file for complete search history.

(56) References Cited

U.S. PATENT DOCUMENTS 5,448,992 A    9/1995 Kupershmidt
(Continued)

FOREIGN PATENT DOCUMENTS

RU    2230485    6/2004
(Continued)

OTHER PUBLICATIONS

Huber, et al.; "The Composition of Perturbing Temperature Fluctuation in Glucose Monitoring Technologies based on Impedance Spectroscopy;" *Medical and Biological Engineering and Computing*; vol. 45, No. 9; Sep. 1, 2007 (863-876).

*Primary Examiner* — Michael D'Angelo
(74) *Attorney, Agent, or Firm* — D. Peter Hochberg; Sean F. Mellino; Richard A. Wolf (57) ABSTRACT

The estimation of the variation of the glucose level in the blood of a person by the variation of the volume of the interstitial fluid compartments in muscular tissue due to a shift of fluid between the extracellular and intracellular compartments caused by variations of the osmotic pressure of the extracellular fluids which is in turn correlated with the glucose level. The variation of the volume of the interstitial fluid compartments is detected by a non-invasive conductometry measurement using electrodes placed in contact with the skin of the person overlying a portion of soft tissue including muscular fibers. To eliminate the adverse effect of the conductivity of the capillary vessels, the conductivity of the tissue is measured independently in two directions, namely parallel and transverse to the muscular fibers.

15 Claims, 5 Drawing Sheets

(56) References Cited

U.S. PATENT DOCUMENTS

| | | |
|---|---|---|
| 7,054,514 B2 | 5/2006 | Uchiyama et al. |
| 7,295,006 B2 | 11/2007 | Potapov et al. |
| 2002/0155615 A1 | 10/2002 | Novikov et al. |
| 2005/0017864 A1* | 1/2005 | Tsoukalis ................ 340/539.12 |
| 2007/0276270 A1* | 11/2007 | Tran .............................. 600/508 |

FOREIGN PATENT DOCUMENTS

| | | |
|---|---|---|
| WO | WO 2007/053963 | 5/2007 |
| WO | WO 2007/075410 | 7/2007 |
| WO | WO 2008/094077 | 8/2008 |

* cited by examiner

NON-INVASIVE METHOD FOR ESTIMATING OF THE VARIATION OF THE GLUCOSE LEVEL IN THE BLOOD OF A PERSON AND APPARATUS FOR CARRYING OUT THE METHOD

CROSS-REFERENCE TO RELATED APPLICATIONS

This application is a National Stage application of International Application No. PCT/EP2009/006178, filed on Aug. 26, 2009, which claims priority of European patent application number 08015256.4, filed on Aug. 29, 2008 and European patent application number 08019159.6, filed on Nov. 3, 2008, all of which are incorporated herein by reference in their entireties.

BACKGROUND OF THE INVENTION

1. Field of the Invention

The present invention relates to a non-invasive method for estimating of the variation of the glucose level $\Delta G$ in the blood of a person and to an apparatus for carrying out the method.

2. Description of the Prior Art

At present, a variety of methods and devices for the non-invasive estimation of blood glucose level are known: laser-light scattering and absorption, combinational (Raman) scattering (U.S. Pat. Nos. 7,054,514, 7,454,429, 5,448,992), nuclear magnetic resonance (NMR) methods (U.S. Pat. No. 7,295,006) and impedance spectroscopy (patents US 2002/0155615, RU 2001/115028). The measuring devices based on such technologies have and most likely will still have a high prime cost and hence a high price non-affordable for an individual consumer.

As affordable and thus promising methods for mass consumption, despite of, strictly speaking, indirect character of blood glucose level estimation, impedance or conductometry methods have been considered. Such methods postulate the presence of a connection between the electrical quantities of tissues and the glucose concentration in blood. However, electric parameters of native tissues are directly dependent not only on glucose or other substances maintenance, but also on the condition of their hydration. Despite of all such known physiological mechanisms, there are still no good and reliable non-invasive glucometers working on the basis of a conductivity measurement.

SUMMARY OF THE PRESENT INVENTION

It is therefore an object of the present invention to provide a reliable method for the non-invasive estimation of the variation of the glucose level in the blood of a person based on a conductometry method. It is a further object of the invention to provide a low cost apparatus for carrying out the inventive method.

These and other objects are achieved by the method of claim 1 and the apparatus of claim 10. Preferred ways of carrying out the invention and preferred embodiments of the inventive apparatus are defined in the dependent claims.

For the estimation of the variation of the glucose level in the blood of a person the present invention uses the variation of the volume of the interstitial fluid compartments in muscular tissue due to a shift of fluid between the extracellular and intracellular compartments caused by variations of the osmotic pressure of the extracellular fluids which is in turn correlated with the glucose level. The extracellular fluids include, besides the interstitial fluid, the blood and lymphe. The glucose level in all such fluids is almost identical.

The osmotic pressure of biological fluids in biological compartments depends on the concentration of substances which are both osmotically active and poorly permeable for plasmatic membranes. Such substances accumulate in one of compartments and equalize the osmolarity level to their own advantage by means of redistribution of water between the compartments. Such substances "pull on water". Glucose is one of these substances in the human body. Membranes of cells have low permeability for glucose. Glucose stays in the extracellular compartments and gets into the cells only with an essential delay.

The variation of the glucose level in the extracellular fluids including the blood plasma is very dynamic. The classical physiological explanation why an organism does not create a mobile power reserve in the form of glucose dissolved in blood, is as follows: the dissolved glucose strongly lifts the osmotic pressure of blood. So, taking into account that tissue fluids of an adult organism contain about 15 g of glucose, it is only enough to supply the organism with power for no more than several tens of minutes. The same figure from the osmotic pressure point of view count up to 5-6 mM/l (mM/l stands for Millimol per liter) from approximately 300, i.e. reaches 2%. Exactly within the accuracy of 2% the osmotic pressure uniformity is maintained in our organism: in case the osmolarity of blood plasma gets a variation limit of more or less than 2%, the organism initiates mechanisms of preservation or deducing of water: the formed secondary urine becomes either essentially hypo- or hyperosmolar. On the other hand, except for exclusive cases of profuse diarrheas, vomit, taking diuretic medicine and the like, we take more than 400 g of glucose in the form of carbohydrates per day, at least 2.5 mol. As a result, glucose in blood "renovates" 25-30 times a day and is very dynamic.

On the other hand, within the cells the concentration of glucose is supported at a rather stable and low level: 1-1.2 mM/l. After getting into a cell, the glucose molecule phosphorylates and becomes glucose-6-phosphate which in turn either "burns down" in reactions of glycolysis or polymerise forming high-molecular glycogen.

Actually, the same laws are true in case of an osmolarity increase of the extracellular compartment due to any another, non "glucose" factor. Sodium is such a factor for example. However, in order to raise the osmolarity of plasmas by 2% by means of sodium, it is necessary to eat approximately 2.5-3 g of sodium chloride—a half of daily norm! In usual conditions we do not eat several grams of table salt and we do not lose electrolytes in same quantities during several tens of minutes. But a usual meal—just one fancy cake—leads exactly to the above mentioned changes of extracellular compartment osmolarity in the most usual ("regular") and not "exclusive" situations. Free amino acids get into the blood and are utilized from it so that their concentration is maintained in the blood at a mM/l level with a high constancy, and fat acids form colloids and so also "hide" their osmotic pressure, being almost absolutely absent in blood in the form of free molecules. Mineral components of the extracellular fluids amount to the main quota of their osmotic pressure level—more than 95%—but they are rather stable in the maintenance in a living organism and their daily circulation is insignificant. A number of examples can be continued, but the conclusion is clear: mainly glucose is in charge of variable component of blood and other extracellular fluids osmotic pressure daily range.

In result, glucose in the cells is maintained at a rather constant level, and outside of the cells, it essentially changes.

It leads to fluctuations of interstitial compartment volume: glucose grows and the volume of interstitial fluids grows as well by water moving from cells to the extracellular compartment, equalizing the osmotic pressure of biological fluid inside and outside the cell.

The variation of the volume of the interstitial fluid compartments is detected according to the invention by means of a non-invasive conductivity measurement using electrodes placed in contact with the skin of the person overlying a portion of soft tissue including muscular fibers.

The conductivity measurements are carried out at least with an alternating current having a relatively low frequency of $1 \times 10^4$ Hz-$5 \cdot \times 10^4$ Hz. Owing to the high active and capacitance resistance of cell membranes, currents of such frequency are mainly ionic currents which spread mainly along the extracellular space enveloping cells and other membranous structures. Their size depends on the eletrolytic composition of the extracellular fluid and the size of its volume or effective sectional area. Dehydrated, freeze-dried tissues are electric insulators and in practice do not carry electrical current.

The blood and lymphe components of the extracellular fluid flow in vessels. A part of the measured conductivity is thereby due to the conductivity of the vessels which are mainly capillary vessels in the tissue of interest for the present invention (such as cross-striped muscles in particular). However, in the human body the volume of the vessels is controlled by various physiological mechanisms of reflex and humoral regulation which support the constancy of the volume of blood circulating in vessels and does not, unlike the volume of the interstitial component, correlate with the osmotic pressure and the glucose level.

To eliminate the adverse effect of the conductivity of the capillary vessels, the invention measures the conductivity of the tissue independently in two directions, namely parallel and transverse to the muscular fibers. Because of the chaotic orientation of the capillary vessels, a variation of the conductivity caused by a variation of the volume of the vessels should be almost equal in both measuring directions. On the other hand, the conductivity parallel to the direction of the muscular fibersis in a larger scale determined by the volume of the interstitial fluid than transverse to the muscular fibers. A variation of the volume of the interstitial compartment thereby has a greater effect on the conductivity parallel than transverse to the muscular fibers.

Using such relationships the invention assumes a variation of the volume of the interstitial compartment to have been effected (by a variation of the osmotic pressure and in turn by a variation of the glucose level in the interstitial fluid) within a given period of time Δt if the relative change of the conductivity measured parallel to the direction of the muscular fibers is larger or smaller than the relative change of the conductivity measured transverse to the muscular fibers. No such change is assumed, if the relative changes of the conductivity measured parallel and transverse to the direction of the muscular fibers are almost identical. In the latter case, the relative changes in conductivity are attributed to changes of the volume of the vessels only.

If the relative change of the conductivity measured parallel to the direction of the muscular fibers is larger than the relative change of the conductivity measured transverse to the direction of the muscular fibers than a positive variation of the glucose level in the interstitial fluid is assumed. If the relative change of the conductivity measured parallel to the direction of the muscular fibers is smaller than the relative change of the conductivity measured transverse to the direction of the muscular fibers than a negative variation of the glucose level in the interstitial fluid is assumed.

The absolute value of the change of the glucose level is estimated to be in the range of 0.15-1.0 μM/1 sec.

The above conductivity changes can be measured with sufficient accuracy within a measuring time interval Δt of not more than 15 seconds, in particular within 2-12 seconds.

There is another adverse effect on the measured conductivities by the contact resistance of the electrodes and the skin surface. Such resistance unfortunately also depends on the blood glucose concentration. An increase of the blood glucose level leads to an increase of the contact resistance by raising the skin surface dryness. Perspiration and hydration become reduced. As a result, the measured conductivity increases as a result of the extracellular fluid volume increase but decreases as a result of the increased contact resistance.

To eliminate the influence of the contact resistance the invention uses a tetrapolar electrode scheme with a pair of outer and a pair of inner electrodes. Current is applied to one pair of such electrodes (preferably to the outer pair) while the voltage is measured between the other pair of electrodes. The elimination of the influence of the contact resistance is due to the fact that the contact resistances of both pairs of electrodes and the skin surface are almost equal and compensate each other. Tetrapolar electrodes are of course used for both measurements parallel and transverse to the muscular fibers.

According to a preferred way of carrying out the invention, the conductometry measurements are carried out additionally with a second alternating current having a relatively high frequency in the range of $0.5 \times 10^6$ Hz-$5 \cdot \times 10^6$ Hz. Currents of such frequency are mainly biasing currents as plasmolemmas are almost transparent for them and the size of such currents depends on the effective sectional area of all tissue fluid, intracellular and extracellular. The additional high frequency measurements are also carried out parallel and transverse to the direction of the muscular fibers of the same tissue of the person and also using the tetrapolar electrodes.

The measured relative changes of the high frequency conductivity are used to obtain a more precise estimation of the variation of the glucose level: It is assumed that there is a greater variation of the glucose level (that has generally been detected by the low frequency measurements) within the period of time Δt if a relative change of the conductivity measured parallel to the direction of the muscular fibers larger or smaller than the relative change of the conductivity measured transverse to the direction of the muscular fibers can also be "seen" in the high frequency. Otherwise, that is when such difference does not occur in the high frequency, the change of the glucose level is assumed to be smaller.

The absolute values of the changes of the glucose level is estimated to be in the range of 0.15-0.5 μM/1 second for the small variation case and in the range of 0.3-1.0 μM/1 second in the larger variation case.

In comparison with the low frequency measurements, the high frequency measurements are less sensitive to variations in the extracellular fluid in relation to all tissue fluid. On the other hand, the electrode/skin-contact is less critical.

According to a further preferred way of carrying out the invention, the temperature of the portion of tissue is additionally measured by means of a temperature sensor in contact with the skin to be able to correct the measured conductivity values for their temperature dependence.

Generally, the specific conductivity of electrolytes such as biological fluids depends on temperature: if the temperature rises, ionic conductivity grows. Now, growth of glucose in blood initiates emission of insulin which is the basic anabolic hormone. The catabolic reactions are temporarily oppressed and as a result, the body temperature decreases. This has a decreasing effect on the conductivity which effect is contrary to the increasing effect of the glucose on the conductivity caused by the extracellular fluid compartment volume growth.

The invention accounts for this effect by measuring the temperature of the skin in the vicinity of the measuring spot with a temperature sensor and by introducing a temperature correction factor to the measured levels of conductivity. Different temperature correction factors are used for the conductivity value correction at high and low frequencies. High frequency conductivity is reduced by 1.5-2.5% per ° C. temperature decrease, while the low frequency conductivity is reduced more than 2 times in relation to high frequency conductivity. The temperature correction factor for the low frequency counts up to 4.5-6.5% per ° C.

For the result of the measurements to be reliable the ambient temperature should not be to extreme (for example lower than −5° C. or higher than 25° C.) and should also not vary too much within a short time. A second temperature sensor can be used for measuring the ambient temperature and for producing a warning signal in such cases for example.

The ranges of frequencies suitable for the present invention have been given above to be between $1 \times 10^4$ Hz-$5 \times 10^4$ Hz for the low frequency and between $0.5 \times 10^6$ Hz-$5 \times 10^6$ Hz for the high frequency. Lowering the low frequency to less than 10 KHz has severe restrictions due to the polarization of electrodes and a dependence of the impedance on the quality of tissue-electrode contact. Increasing the high frequency up to 10 MHz and more leads to inductive and capacitor (jet) disturbances: the conductivity depends on the position of surrounding elements, their size and conductivity.

Finding out the correct and/or best measuring orientations for the tetrapolar electrode devices at a specific spot of tissue of a person can be assisted by using eight tetrapolar electrode devices instead of just two. The eight tetrapolar electrode devices are placed in contact with the skin of said person at said spot oriented along eight axis forming a radially symmetric scheme. A conductivity value of said tissue is measured with each one of said eight tetrapolar electrode devices to define the axis with minimal conductivity and the axis with maximal conductivity. The tetrapolar electrode device oriented along the axis with maximal conductivity is then used for the measurement along the direction of the muscular fibers. Likewise, the tetrapolar electrode device oriented along the axis with minimal conductivity is then used for the measurement transverse to the direction of the muscular fibers.

In this way the correct and/or best measuring orientations reflecting the anisotropy of the conductivity of the tissue need not to be entered a priori—according to anatomical (muscular or vascular) landmarks—but are defined a posteriori—as a result of a measurement. In this way the inventive method can correctly even be applied by persons having no knowledge about said anatomical landmarks at the spot of tissue at which they want to carry out the method.

BRIEF DESCRIPTION OF THE DRAWINGS

Embodiments and preferred ways of carrying out the invention shall be described in the following with reference to the accompanying drawings, wherein.

DETAILED DESCRIPTION OF THE PRESENT INVENTION

Figure 1:
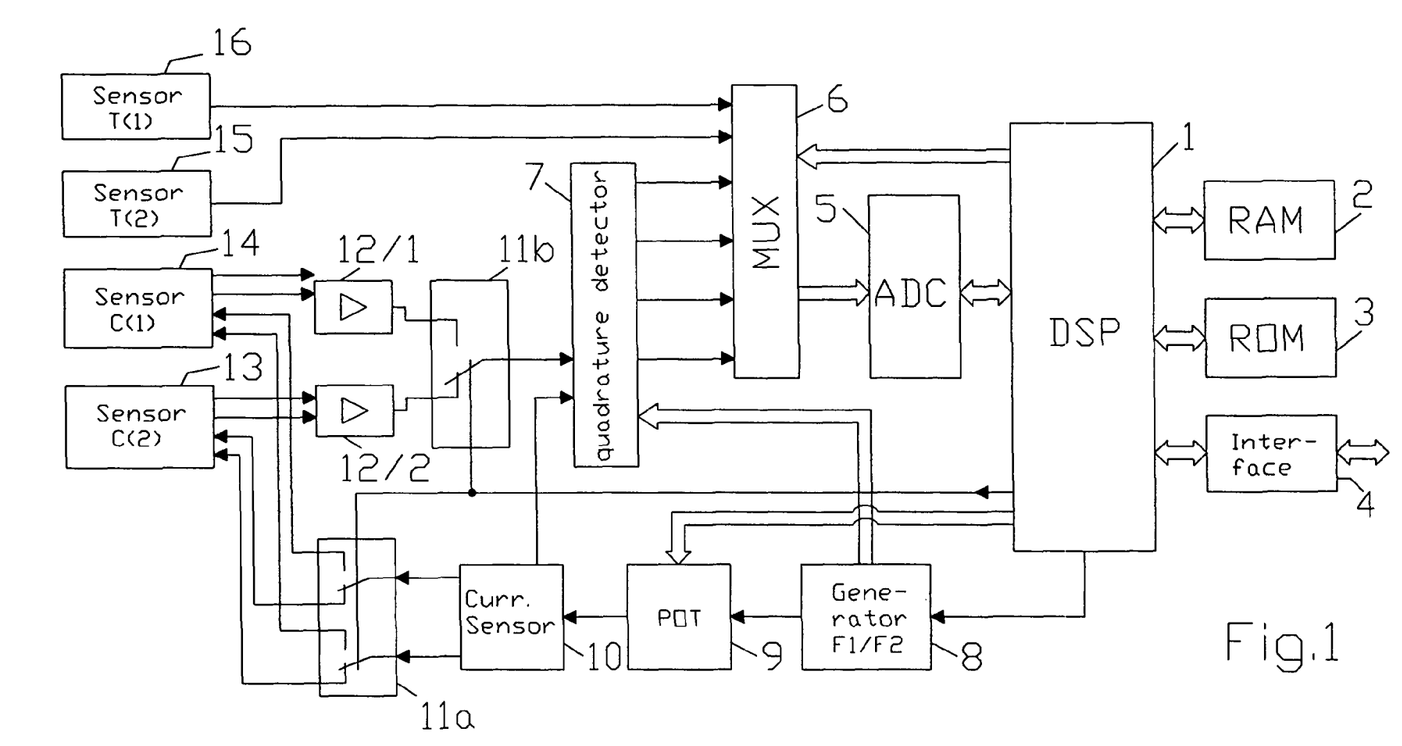
FIG. 1 is a block diagram of the present invention having two conductivity sensors.

The apparatus of FIG. 1 comprises: a digital signal processor (DSP) 1, a random access memory (RAM) 2, a read-only memory (ROM) 3, a computer input-output (Interface RS232) 4, an analog-to-digital converter (ADC) 5, a multiplexer (MUX) 6, a quadrature detector 7, a double-frequency oscillator 8, a digital potentiometer 9, a current sensor 10, two conductivity sensor switches 11a and 11b, two difference amplifiers 12/1 and 12/2, two sensors of conductivity 13 and 14 and two temperature sensors 15 and 16.

The digital signal processor 1 operates the process of measurement, accepts the results of measurements coming from the analog-to-digital converter 5, makes preliminary processing of signals and transfers them to an external computer or PDA (not shown and being not an integral part of the apparatus) through interface 4. The processor operating program is stored in the reprogrammable read-only memory (ROM) 3.

The apparatus works as follows: oscillator 8 interchangeably forms a. c. alternating voltages with F1 (30 khz) and F2 (1 MHz) frequencies. Such voltages go through digital potentiometer 9, current sensor 10 and switching device 11a which interchangeably connects the voltages to the current-input electrodes "IN" (FIG. 3) of sensors 13 and 14. Oscillator 8 also forms control signals which are applied to quadrature detector 7 for synchronization purposes.

The digital potentiometer 9, controlled by processor 1, automatically supports amplitudes of voltage on the current-carrying electrodes "IN" (FIG. 3) of conductivity sensors 13 and 14 which are suitable for the individual person's initial skin contact resistance. It allows to expand a dynamic range of conductivity measurements and to increase measurements accuracy.

Signals from the central electrodes "OUT" (FIG. 2) of the conductivity sensors 13 and 14 are amplified by difference amplifiers 12 and, through the second conductivity sensor switch 11b, get to one of the inputs identified by U~ of the quadrature detector 7. A voltage proportional to the current on the current-carrying electrodes "IN" (FIG. 3) is applied from current sensor 10 to a second input identified by I~ of the quadrature detector 7.

Quadrature detector 7 has four outputs. At the output identified by $U_0^2$ quadrature detector 7 provides a DC signal which is proportional to the square of the AC signal at its input identified by U~ at a time $t_0$. At the output identified by $U_{\pi/2}^2$ quadrature detector 7 provides a DC signal which is proportional to the square of the AC signal at its input identified by U~ at the time $t_{\pi/2}$. At the output identified by $I_0^2$ quadrature detector 7 provides a DC signal which is proportional to the square of the AC signal at its input identified by I~ at a time $t_0$. At the output identified by $I_{\pi/2}^2$ quadrature detector 7 provides a DC signal which is proportional to the square of the AC signal at its input identified by I~ at the time $t_{\pi/2}$.

Such DC signals get, through multiplexer (MUX) 6 and analog-to-digital converter (ADC) 5, by which they are digitized, to digital signal processor (DSP) 1.

Continuous voltages from the two temperature sensors 15 and 16 also get through multiplexer 6 and analog-to-digital converter 5 in digitized form to the digital signal processor (DSP) 1.

The digital signal processor (DSP) 1 calculates average values U and I from the four output signals of the quadrature detector 7 as follows:

$$U=\text{SQRT}(U_O^2+U_{\pi/2}^2)$$

$$I=\text{SQRT}(I_O^2+I_{\pi/2}^2)$$

and calculates conductivity values from such average values U and I by $$C=I/U$$

Such conductivity values are further corrected using the temperature values obtained by temperature sensor 15.

Depending on the temperature values obtained by temperature sensor 16 a warning signal may also be created by digital signal processor (DSP) 1.

Figure 2:
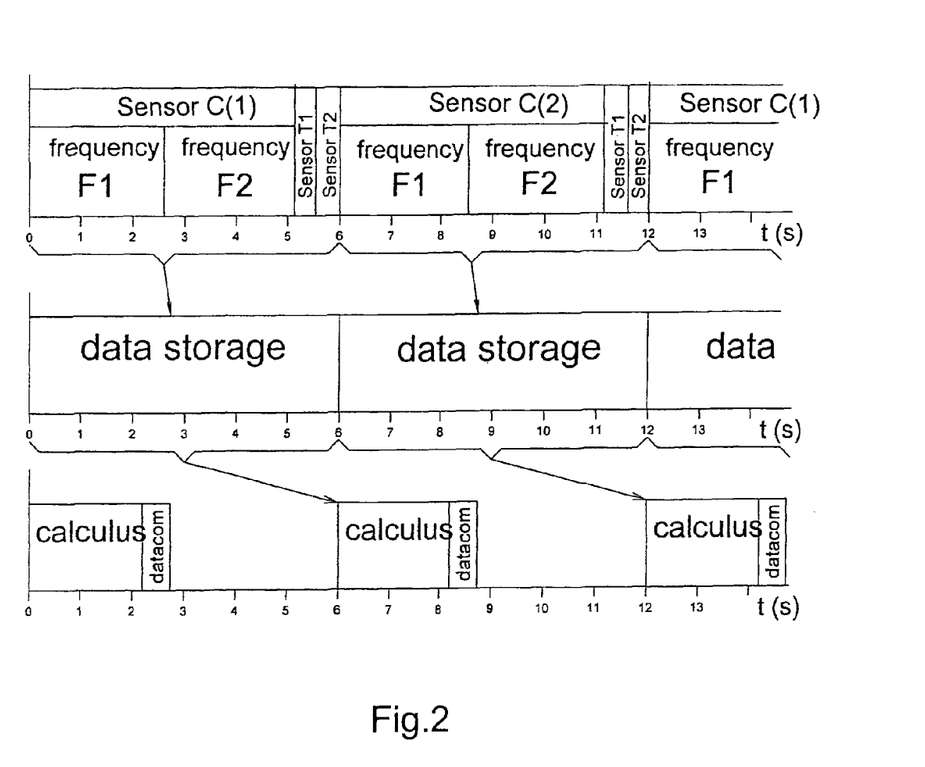
FIG. 2 is a time diagram showing a measuring cycle.

The apparatus operates cyclically. FIG. 2 shows a full cycle and a part of a following cycle.

A cycle starts with input U~ of the quadrature detector 7 being connected to sensor 13 by means of the second conductivity sensor switch 11b. Double-frequency oscillator 8 first produces frequency F1 which is applied by means of the first conductivity sensor switch 11a to sensor 13. Then double-frequency oscillator 8 produces frequency F2 which is also applied by means of the first conductivity sensor switch 11a to sensor 13. In the following temperature values from temperatures sensors 15 and 16 are obtained, respectively, this finishing the first half of the cycle. In the second half-cycle the individual steps of the first half-cycle are repeated with the difference, that frequencies F1 and F2 are applied by means of the first conductivity sensor switch 11a to sensor 14. In addition, input U~ of the quadrature detector 7 is also connected to sensor 14 by means of the second conductivity sensor switch 11b.

Data storage, preliminary processing of previously collected data and transmission of data to the computer is performed as this is also indicated in FIG. 2.

In the example of FIG. 2 a full cycle of high- and low-frequency conductivity measurement on both sensors takes 12 seconds. It is to be understood that this cycle is just exemplary but may still be reduced to only a few seconds.

The apparatus may be powered by a rechargeable battery.

Figure 3:
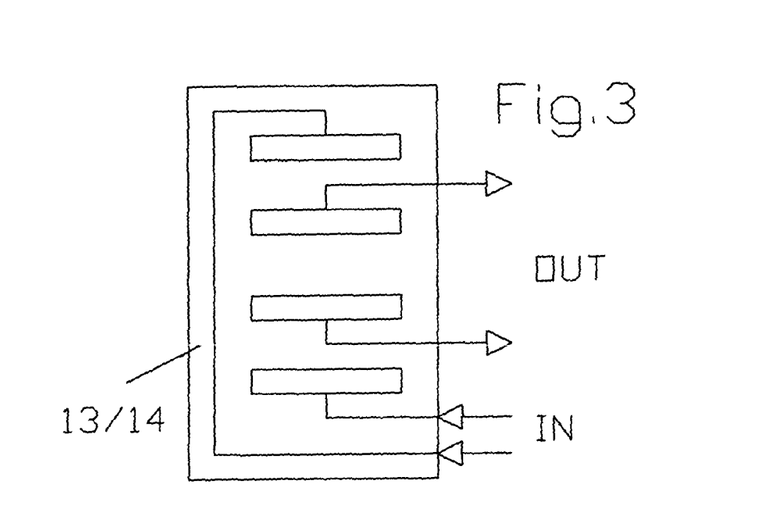
FIG. 3 is a diagrammatic representation of either one of the two conductivity sensors of the apparatus of FIG. 1.
Figure 4:
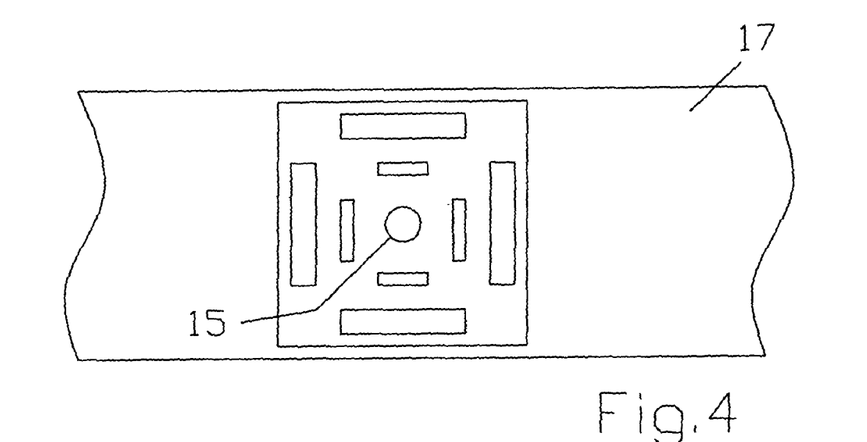
FIG. 4 is a representation of the preferred relative geometrical arrangement of the electrodes of the two conductivity sensors.

A tetrapolar electrode scheme is used for both conductivity sensors 13 and 14. The relative position of the "IN" and "OUT" electrodes of such type of sensor is shown in FIG. 3. FIG. 4 shows the preferred mutual-perpendicular arrangement of the tetrapolar electrodes of both sensors 13 and 14 on a common planar base. Temperature sensor 15 is positioned in the center of the eight electrodes on the same base. The base may be formed by a cuff suitable for being affixed to an arm of a patient for example.

Figure 5:
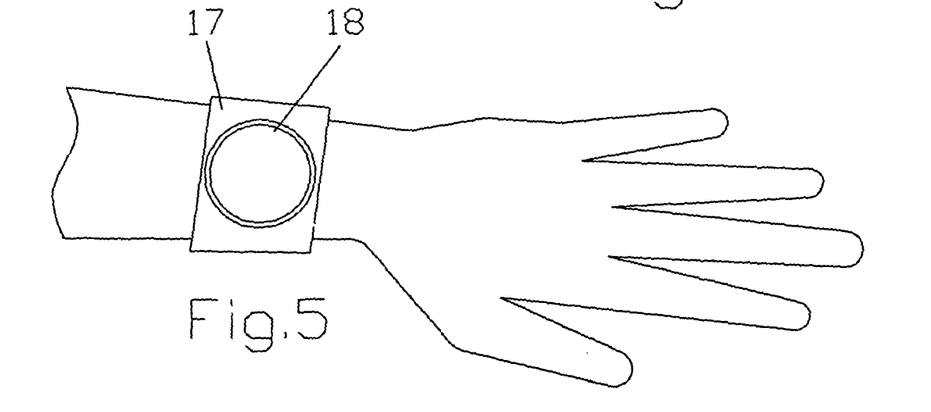
FIG. 5 is a representation of an arm of a patient with at least a part of the apparatus of FIG. 1 attached thereto by means of a cuff.

FIG. 5 shows an arm of a patient to which such a cuff 17 is affixed with the non-visible electrodes of sensors 13 and 14 and the non-visible temperature sensor 15 on the inner side thereof in skin-contact. On the outward side of the cuff 17 a small casing 18 is provided which preferably houses the above described electronic components of the inventive apparatus as well as the batteries. The described data transfer to a computer may be achieved via a cable connection between the casing and the computer or even wireless.

It is to be understood that measuring at an arm is only exemplary and that measuring at any other spot of the human body overlying soft muscular tissue would also be possible.

In particular in the embodiment as described above the inventive apparatus can be carried easily and without serious disturbances to the comfort of the carrying person for several hours including night and sleeping times. Thereby, the measuring cycle is repeated steadily.

Figure 6:
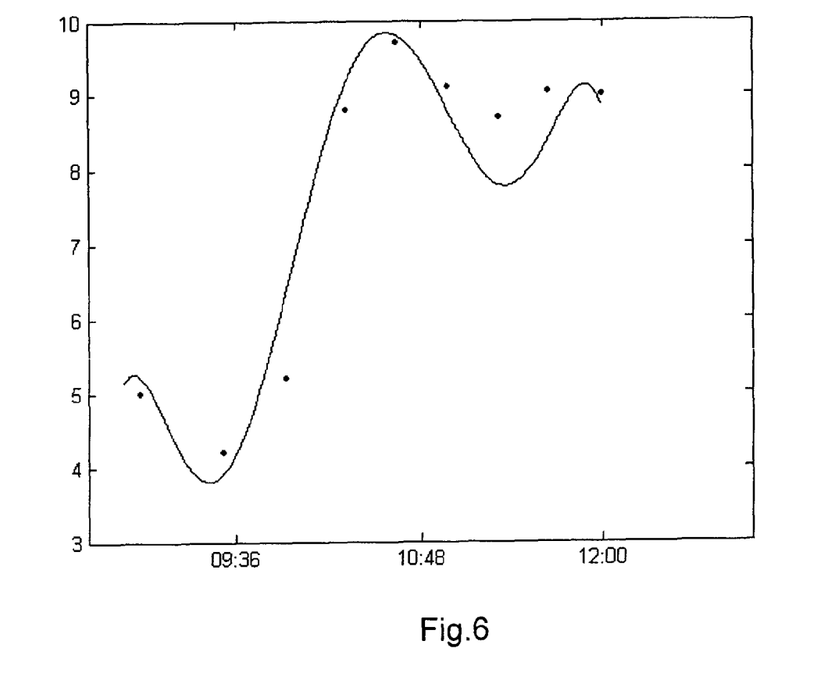
FIGS. 6-8 are time diagrams showing the variation of the glucose level of three patients obtained in accordance with the present invention in comparison with data obtained by a conventional invasive measuring system.
Figure 7:
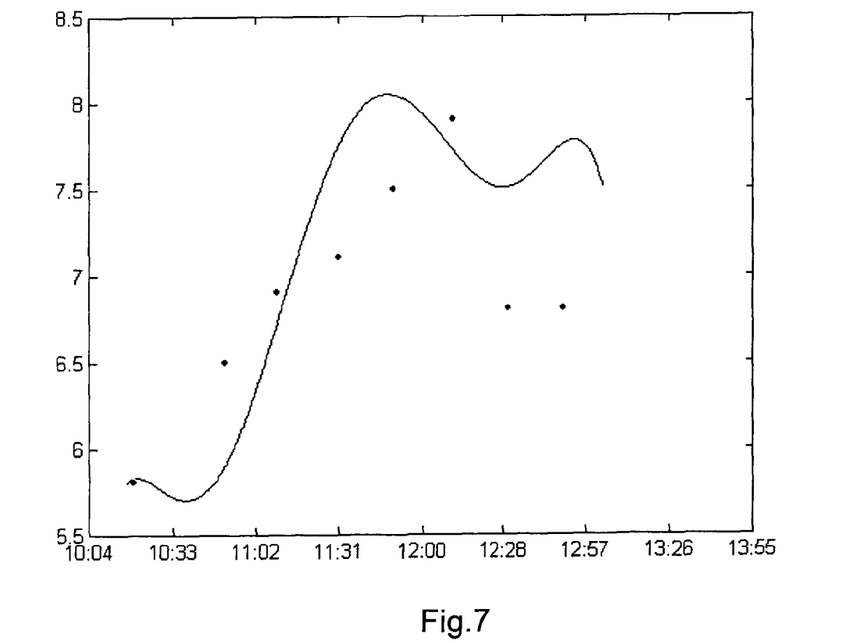
Figure 8:
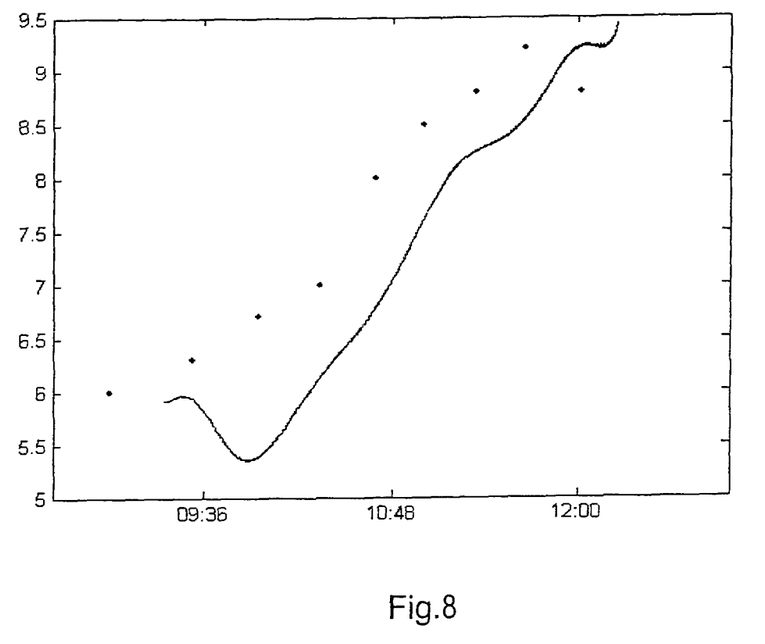

Starting from some point in time the variation of the glucose level in the blood can be monitored and preferably stored for being shown in a time diagram. FIGS. 6-8 are such time diagrams showing the variation of the glucose level of three patients having Diabetes II over several hours each obtained in accordance with the present invention. The axis of abscissae represents the time in hours. The axis of ordinates represents the concentration of glucose in mmol/l.

It is to be noted that the invention only provides the variation of the glucose level but no absolute values. To obtain absolute values some calibration is required which may be achieved for example at the beginning of a measurement period by means of a standard invasive method.

In the diagrams of FIGS. 6-8 glucose values obtained by the well known and widely used ACCU CHECK® System are shown for comparison.

FIG. 6 shows a glucose tolerance test carried out with a female patient of the age of 49. The patient took 70 g of glucose per 130 ml of water between 09:51 and 09:52.

FIG. 7 shows the variation of the glucose level in the blood of a male patient of the age of 81 after a meal between 10:40 and 10:48.

FIG. 8 shows the variation of the glucose level in the blood of a female patient of the age of 69 after a meal between 10:00 and 10:05.

The curves of FIGS. 6-8, though originally being step curves, have been polynomically smoothed to better show the overall trend of the glucose level variation.

Figure 9:
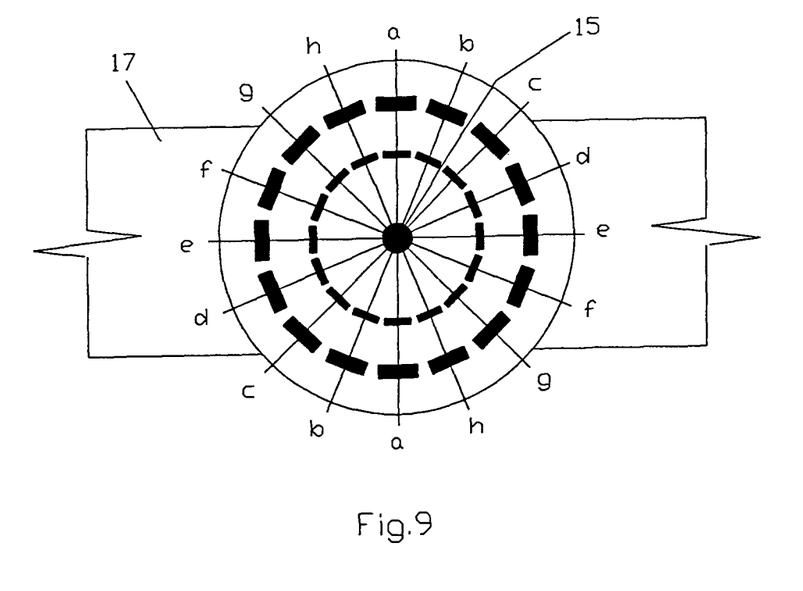
FIG. 9 is a representation of the preferred relative geometrical arrangement of the electrodes of in total eight conductivity sensors for use in a preferred embodiment of the present invention.

As already described, FIG. 4 shows a preferred mutual arrangement of the tetrapolar electrodes of sensors 13 and 14 on a common planar base. FIG. 9 shows the arrangement of the tetrapolar electrodes of in total eight sensors on a common planar base according to an even more preferred embodiment of the present invention. The four electrodes of each one of the eight sensors are arranged along eight axis a-h forming a radially symmetric scheme. A temperature sensor 15 is again positioned in the center of the scheme at the axis of rotation thereof, such center being also the center of all tetrapolar electrode devices. As in FIG. 4 and FIG. 5, the base may be formed by a cuff 17 suitable for being affixed to an arm of a patient.

With the arrangement of FIG. 9 the directions with the highest conductivity differential can automatically be found. For this, an initial testing measurement is carried out consecutively along each axis a-h to define the axis with maximal conductivity and the axis with minimal conductivity. The sensor which is oriented along the axis along which the conductivity is maximal is then used like sensor 13 of FIG. 1. Likewise, the sensor which is oriented along the axis along which the conductivity is minimal is then used like sensor 14 of FIG. 1.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A noninvasive method for estimating a variation of glucose level $\Delta G$ in the blood of a person within a time interval $\Delta t$, comprising the following steps:
   placing a first tetrapolar electrode device in contact with skin of the person overlying a portion of soft tissue including muscular fibers oriented parallel to the direction of the muscular fibers;
   placing a second tetrapolar electrode device in contact with the skin of said person overlying said portion of soft tissue oriented transverse to the direction of the muscular fibers;
   measuring for a time interval $\Delta t$:
      with the first tetrapolar electron device a relative variation $\Delta C_{\|,LF}/C_{\|,LF}$ of the conductivity value $C_{\|,LF}$ of said tissue parallel to the direction of the muscular fibers at a low frequency;
      with the second tetrapolar electron device a relative variation $\Delta C_{\perp,LF}/C_{\perp,LF}$ of a conductivity value $C_{\perp,LF}$ of said tissue transverse to the direction of the muscular fibers at said low frequency;
   estimating $\Delta G$ by a processing apparatus as:

$0.0$ if $\Delta C_{\|,LF}/C_{\|,LF} \approx \Delta C_{\perp,LF}/C_{\perp,LF}$ $+a$ if $\Delta C_{\|,LF}/C_{\|,LF} > \Delta C_{\perp,LF}/C_{\perp,LF}$ $-a$ if $\Delta C_{\|,LF}/C_{\|,LF} < \Delta C_{\perp,LF}/C_{\perp,LF}$ wherein:
   a is in the range of 0.15-1.0 μM/l sec;
   the low frequency is in the range of $1 \cdot \times 10^4$ Hz-$5 \cdot \times 10^4$ Hz; and
   "$\approx$" means "equal within a range of $+/-2.5\%$-$+/-7.5\%$".

2. The method according to claim 1, wherein $\Delta t$ is in the range of not more than 15 seconds.

3. The method according to claim 1, further comprising the following steps:
   measuring for the time interval $\Delta t$:
      with the first tetrapolar electron device a relative variation $\Delta C_{\|,HF}/C_{\|,HF}$ of a conductivity value $C_{\|,HF}$ of said tissue parallel to the direction of the muscular fibers at a high frequency;
      with the second tetrapolar electron device the relative variation $\Delta C_{\perp,HF}/C_{\perp,HF}$ of the conductivity value $C_{\perp,HF}$ of said tissue transverse to the direction of the muscular fibers at said high frequency;
   estimating $\Delta G$ by a processing apparatus as:

$+a$ if $\Delta C_{\|,LF}/C_{\|,LF} > \Delta C_{\perp,LF}/C_{\perp,LF}$ and $\Delta C_{\|,HF}/C_{\|,HF} \approx \Delta C_{\perp,HF}/C_{\perp,HF}$ $+b$ if $\Delta C_{\|,LF}/C_{\|,LF} > \Delta C_{\perp,LF}/C_{\perp,LF}$ and $\Delta C_{\|,HF}/C_{\|,HF} > \Delta C_{\perp,HF}/C_{\perp,HF}$ $-a$ if $\Delta C_{\|,LF}/C_{\|,LF} < \Delta C_{\perp,LF}/C_{\perp,LF}$ and $\Delta C_{\|,HF}/C_{\|,HF} \approx \Delta C_{\perp,HF}/C_{\perp,HF}$; and $-b$ if $\Delta C_{\|,LF}/C_{\|,LF} < \Delta C_{\perp,LF}/C_{\perp,LF}$ and $\Delta C_{\|,HF}/C_{\|,HF} < \Delta C_{\perp,HF}/C_{\perp,HF}$;

wherein:
   a is in the range of 0.15-0.5 μM/l second;
   b is in the range of 0.3-1.0 μM/l second; and
   the high frequency is in the range of $0.5 \cdot \times 10^6$ Hz-$5 \cdot \times 10^6$ Hz.

4. The method according to claim 1, and further comprising the steps of:
   providing a pair of inner electrodes and a pair of outer electrodes to said tetrapolar electrode devices;
   applying alternating currents having said low or high frequency to one of the pairs of electrodes of said tetrapolar electrode devices for obtaining impedance values, and
   measuring the alternating voltages resulting from such currents at the other one of the pairs of electrodes.

5. The method according to claim 4, wherein the conductivity values C are obtained by calculation from the applied alternating currents and the measured alternating voltages after rectification and digitizing.

6. The method according to claim 1, further comprising the steps of:
   placing a temperature sensor in contact with the skin of said person overlying said portion of soft tissue;
   measuring the temperature T of the skin; and
   correcting the conductivity values by a factor f,
   wherein:
   f is a reduction factor in case of a temperature decrease;
   f is in the range of 4.5-6.5% per ° C. temperature difference from $T_0$ for the low frequency measurements; and
   $T_0$ is a previously measured temperature of the skin of said person overlying said portion of soft tissue.

7. The method according to claim 6, wherein f is in the range of 1.5-2.5% per ° C. temperature difference from $T_0$ for the high frequency measurements.

8. The method according to claim 6, wherein the measured temperature T of the skin is digitized and correction of the conductivity values by said factor f is carried out by calculation.

9. The method according to claim 1, wherein the steps of placing the first tetrapolar electrode device in contact with the skin of the person overlying a portion of soft tissue including muscular fibers oriented parallel to the direction of the muscular fibers and placing the second tetrapolar electrode device in contact with the skin of the person overlying said portion of soft tissue oriented transverse to the direction of the muscular fibers include the following steps:
   placing eight tetrapolar electron devices in contact with the skin of the person overlying said portion of soft tissue oriented along eight axes forming a radially symmetric scheme;
   measuring a conductivity value of said tissue with each one of said eight tetrapolar electron devices to define the axis with minimal conductivity and the axis with maximal conductivity;
   using the tetrapolar electrode device oriented along the axis with maximal conductivity as the first tetrapolar electrode device; and
   using the tetrapolar electrode device oriented along the axis with minimal conductivity as the second tetrapolar electrode device.

10. An apparatus for estimating a variation of glucose level $\Delta G$ in the blood of a person within a time interval $\Delta t$, comprising;
    a first tetrapolar electrode device in contact with skin of the person overlying a portion of soft tissue including muscular fibers oriented parallel to the direction of the muscular fibers;
    a second tetrapolar electrode device in contact with the skin of said person overlying said portion of soft tissue oriented transverse to the direction of the muscular fibers;
    a processing apparatus for measuring for a time interval $\Delta t$:

with the first tetrapolar electron device a relative variation $\Delta C_{\parallel,LF}/C_{\parallel,LF}$ of the conductivity value $C_{\parallel,LF}$ of said tissue parallel to the direction of the muscular fibers at a low frequency;

with the second tetrapolar electron device a relative variation $\Delta C_{\perp,LF}/C_{\perp,LF}$ of a conductivity value $C_{\parallel,LF}$ of said tissue transverse to the direction of the muscular fibers at said low frequency;

estimating AG by the processing apparatus as:

$0.0$ if $\Delta C_{\parallel,LF}/C_{\parallel,LF} \approx \Delta C_{\perp,LF}/C_{\perp,LF}$ $+a$ if $\Delta C_{\parallel,LF}/C_{\parallel,LF} > \Delta C_{\perp,LF}/C_{\perp,LF}$ $-a$ if $\Delta C_{\parallel,LF}/C_{\parallel,LF} < \Delta C_{\perp,LF}/C_{\perp,LF}$ wherein:
a is in the range of 0.15-1.0 µM/l sec;
the low frequency is in the range of $1 \cdot \times 10^4$ Hz-$5 \cdot \times 10^4$ Hz; and
"$\approx$" means "equal within a range of +/−2.5%-+/−7.5%".

11. The apparatus according to claim 10, further comprising having eight tetrapolar electrode devices oriented along eight axis forming a radially symmetric scheme.

12. The apparatus according to claim 10, further comprising a device for generating alternating currents.

13. The apparatus according to claim 10, further comprising a device for rectifying said alternating currents and measured alternating voltages, for digitizing rectified currents and rectified voltages and for processing digitized data.

14. The apparatus according to claim 13, further comprising a device for transmitting processed data to an external data processing apparatus.

15. The apparatus according to claim 10, further comprising a temperature sensor, wherein the temperature sensor is located in the center of the tetrapolar electrode devices.

* * * * *